US010889852B2

(12) United States Patent
Molloy et al.

(10) Patent No.: US 10,889,852 B2
(45) Date of Patent: Jan. 12, 2021

(54) GENOME METHYLATION ANALYSIS

(71) Applicant: Commonwealth Scientific and Industrial Research Organisation, Campbell (AU)

(72) Inventors: Peter Molloy, Chatswood (AU); Susan Margaret Mitchell, Gladesville (AU); Konsta Duesing, Campbell (AU)

(73) Assignee: Commonwealth Scientific and Industrial Research Organisation, Act (AU)

( * ) Notice: Subject to any disclaimer, the term of this patent is extended or adjusted under 35 U.S.C. 154(b) by 0 days.

(21) Appl. No.: 15/519,893

(22) PCT Filed: Oct. 20, 2015

(86) PCT No.: PCT/AU2015/050646
§ 371 (c)(1),
(2) Date: Apr. 18, 2017

(87) PCT Pub. No.: WO2016/061624
PCT Pub. Date: Apr. 28, 2016

(65) Prior Publication Data
US 2017/0247748 A1     Aug. 31, 2017

(30) Foreign Application Priority Data
Oct. 20, 2014 (AU) .............................. 2014904189

(51) Int. Cl.
*C12Q 1/6809* (2018.01)
*C12Q 1/6869* (2018.01)
(Continued)

(52) U.S. Cl.
CPC ......... *C12Q 1/6809* (2013.01); *C12Q 1/6806* (2013.01); *C12Q 1/6869* (2013.01);
(Continued)

(58) Field of Classification Search
CPC .. C12Q 1/6809; C12Q 1/6806; C12Q 1/6883; C12Q 1/6869; C12Q 2600/118; C12Q 2600/154; G16B 30/00
See application file for complete search history.

(56) References Cited

U.S. PATENT DOCUMENTS

2003/0157546 A1* 8/2003 McCombie .......... C12Q 1/6809
                                                          435/6.11
2005/0153316 A1* 7/2005 Jeddeloh ................ C12Q 1/683
                                                          435/6.12
(Continued)

FOREIGN PATENT DOCUMENTS

CN      103233072      8/2013
WO      02/060318      8/2002
(Continued)

OTHER PUBLICATIONS

Brunner et al. Genome Research. 2009. 19(6):1044-1056. (Year: 2009).*
(Continued)

*Primary Examiner* — Joseph G. Dauner
(74) *Attorney, Agent, or Firm* — Merchant & Gould PC

(57) ABSTRACT

Provided herein are methods for identifying sites and regions within a gene or genome that are amenable to analysis of methylation. The methods disclosed herein allow the efficient identification on a genome-wide scale of target restriction sites and fragments that provide targets for subsequent analysis.

16 Claims, 7 Drawing Sheets
Specification includes a Sequence Listing.

(51) Int. Cl.
C12Q 1/6806 (2018.01)
C12Q 1/6883 (2018.01)
G16B 30/00 (2019.01)

(52) U.S. Cl.
CPC ........... *C12Q 1/6883* (2013.01); *G16B 30/00* (2019.02); *C12Q 2600/118* (2013.01); *C12Q 2600/154* (2013.01)

(56) References Cited

U.S. PATENT DOCUMENTS

| | | | | |
|---|---|---|---|---|
| 2005/0202490 A1* | 9/2005 | Makarov | ............ | C12N 15/1072 435/6.12 |
| 2006/0286585 A1* | 12/2006 | Skinner | ................ | A01K 67/027 435/6.11 |
| 2008/0108073 A1* | 5/2008 | Nautiyal | .............. | C12Q 1/6813 435/6.12 |

FOREIGN PATENT DOCUMENTS

| WO | 2010/085774 A1 | 7/2010 |
|---|---|---|
| WO | 2013/097060 | 4/2013 |

OTHER PUBLICATIONS

Gonchar et al. Translated from Ovchinnikov bulletin of biotechnology and physical and chemical biology. 2010. 6(1):5-12. (Year: 2010).*

Abdurashitov et al. BMC Genomics. 2009. 10:322, 10 pages. (Year: 2009).*

Zemlyanskaya et al. Molecular Biology. 2013. 47:784-795. (Year: 2013).*

Sandoval et al. "Validation of a DNA methylation microarray for 450,00 CpG sites in the human genome." Epigentics 6:6 (2011) pp. 692-702.

Rand et al. "Sensitive and selectrive amplification of methylated DNA sequences using helper-dependent chain reaction in combitnation with a methylation-dependent restriction enzymes." Nucleic Acids Research, vol. 41, No. 1. (2013) pp. 1-10.

Clark et al. "DNA methylation: Bisulphite modification and analysis." Nature Protocols, vol. 1, No. 5 (2006) pp. 2353-2364.

Cottrell et al. "A real-time PCR assay for DNA-methylation using methylation-specific blockers." Nucleic Acids Research, vol. 32, No. 1 (2004) pp. 1-8.

Eads et al. "MethyLight: a high-throughput assay to measure DNA methylation." Nucleic Acids Research, vol. 28, No. 8. (2000) pp. 1-8.

Geiss et al. "Direct multiplexed measurement of gene expression with color-coded probe pairs." Nature Biotechnology, vol. 26, No. 3 (2008) pp. 317-326.

Herman et al. "Methylation-specific PCR: A novel PCR assay for methylation status of CpG islands." Proc Natl Acad Sci, vol. 93 (1996) pp. 9821-9826.

Lofton-Day et al. "DNA Methylation Biomarkers for Blood-based colorectal cancer screening." Clinical Chemistry, vol. 54, No. 2, (2008) pp. 414-423.

Malley et al. "A distinct region of the MGMT CpG island critical for transcriptional regulation is preferntially methylated in glioblastoma cells and xenografts." Acta Neuropathal, vol. 121 (2011) pp. 651-661.

Tarasova et al. "Substrate specificty of new methyl-directed DNA endonuclease GlaI." BMC Molecular Biology vol. 9, Issue 7, 2008.

Meissner et al. "Genome-scale DNA methylation maps of pluripotent and differentiated cells." Nature Letters vol. 454, No. 7 (2008) pp. 766-771.

Rand et al. "Conversion-specific detection of DNA methylation using real-time polymerase chain reaction (ConLight-MSP) to avoid false positives." Methods, vol. 27 (2002) pp. 114-120.

Rand et al. "Sensitive measurements of unmethylated repeat DNA sequences by end-specific PCR" Biotechniques vol. 49, No. 4 (2010) pp. xiii-xvii.

Rand et al. "Fleadloop suprression PCR and its applications to selective amplification of methylated DNA sequences." Nucleic Acids Research, vol. 33, No. 14 (2005) pp. 1-11.

Weisenberger et al. "CpG island methylator phenotyp underlies sporadic microsatellite instability and is tightly associated with BRAF mutation in colorectal cancer." Nature Genetics, vol. 38, No. 7 (2006) pp. 787-793.

International Search Report for International Application No. PCT/AU2015/050646 dated Dec. 7, 2015 (5 pages).

International Written Opinion for International Application No. PCT/AU2015/050646 dated Dec. 7, 2015 (5 pages).

Huang et al. "High-throughput sequencing of methylated cytosine enriched by modification-dependent restriction endonuclease MspJI." BMC Genetics, vol. 14, No. 56 (2013) pp. 1-9.

Rand et al. "Sensitive measurement of unmethylated repeat DNA sequence by end-specific PCR." BioTechniques Focus: Epigentics, vol. 49, No. 4. Oct. 2010, pp. Xiii-Xvii.

Rand et al. "Sensitive and selective amplification of methylated DNA sequences using helper-dependent chain reaction in combination with a methylation-dependent restriction ensymes." Nucleic Acids Research. 2012, pp. 1-10.

Huang et al. "High-throughput sequencing of methylated cytosine enriched by modification-dependent restriction endonuclease MspJI." BMC Genetics, vol. 14, No. 45, 2013, pp. 1-9.

Xin et al. "Methyl-Analyzer-whole genome DNA methylation profiling." Bioinformatics, vol. 27, No. 16, 2011, pp. 2296-2297.

Supplemental European Search Report for EP Application No. 15 85 2545 dated Feb. 6, 2018 (pp. 1-8).

* cited by examiner

A

B

GENOME METHYLATION ANALYSIS

This application is a U.S. National Stage Application under 35 U.S.C. § 371 of International Patent Application No. PCT/AU2015/050646 filed Oct. 20, 2015, which claims the benefit of priority to Australian Patent Application No. 2014904189 filed Oct. 20, 2014, the disclosures of all of which are hereby incorporated by reference in their entireties. The International Application was published in English on Apr. 28, 2016 as WO 2016/061624.

FIELD OF THE INVENTION

The present invention relates generally to methods for identifying sites and regions within a gene or genome that are amenable to analysis of methylation, for use, for example, in diagnostic or prognostic assays of disease.

BACKGROUND OF THE INVENTION

In addition to the four standard bases, adenine, guanine, cytosine and thymine, the genomes of most organisms contain modified bases that are commonly added enzymatically after DNA replication. The most common modified bases are 5-methylcytosine (meC) and 6-methyladenosine. The genomes of most plants and animals contain meC, generally found in the context of CpG dinucleotides or CpNpG trinucleotides. Site-specific DNA methylation is involved in processes that range from host defence mechanisms and DNA repair in bacteria to control of gene regulation and developmental programming in higher organisms. In vertebrates, DNA methylation patterns characteristic of different cell types are established during development.

Methylation of cytosine residues in DNA plays an important role in gene regulation, the consequence typically being gene silencing. Abnormal methylation is a hallmark of many cancers such as colorectal cancer, and is increasingly being recognized as a factor in a variety of other conditions and disease states including conditions associated with aging such as Alzheimer's disease, metabolic diseases such as obesity and metabolic syndrome, arthritis and cardiovascular disease such as atherosclerosis and associated conditions.

Accordingly, there has been enormous interest in the development of methods and assays that can selectively amplify methylated DNA sequences, both for quantifying the proportion of methylated DNA in a sample or for the sensitive detection of methylated DNA sequences in a biological sample (see, for example, Lofton-Day et al., 2008).

The most commonly used methods, amenable to the detection of small amounts of methylated DNA and for its selective amplification, rely on chemical modification of DNA with sodium bisulphite, to convert cytosines to uracils while leaving meC unreacted. After bisulphite treatment, the sequence differences between methylated and unmethylated DNAs in turn allow for various methods of sequence specific analysis of DNA methylation patterns (Clark et al., 2006).

Such selective amplification methods include Methylation Specific PCR (MSP) (Herman et al., 1996), HeavyMethyl PCR (Cottrell et al., 2004) and Headloop PCR (Rand et al., 2005). MSP assays (or MethyLight (Eads et al., 2000) or ConLight (Rand et al., 2002) assays that use fluorescent probes) can be used in combination with a reference, non-methylation-sensitive PCR, to quantify the proportion of methylated DNA (PMR) within a sample (Weisenberger et al., 2006). While such assays are widely used, the bisulphite reaction adds time and cost to analyses and can lead to loss of some DNA, especially with small DNA inputs as might be encountered in clinical samples.

Assays that use methylation-sensitive restriction enzymes have also been developed. These assays use primers flanking one or more methylation-sensitive enzyme restriction sites. After digestion with the methylation-sensitive enzyme, uncut methylated DNA can be amplified, but not DNA that has been cut at any unmethylated CpG site between the primers. Failure to digest, or incomplete digestion of, unmethylated DNA can lead to false positive signals. As a result such assays have not become widely used, especially in a clinical context.

In many instances it is desirable to develop assays for amplification of sequences that are differentially methylated in one condition compared to another, such as in cancer compared to normal tissue, or to distinguish cancers that will be responsive to a drug treatment or intervention. Of potential benefit in such assays is the recent identification of restriction enzymes that cut DNA only when cytosines within their recognition sites are methylated, such that after digestion, free DNA ends are only produced when a particular site is methylated. This provides the opportunity to positively select for amplification based on these cut ends. However, disadvantages of such methylation-dependent enzymes is that the efficiency of cutting at particular sequences can be dependent both on the sequence at the recognition site and the number of methylated cytosines (e.g. GlaI), or intermediate cutting may occur depending on the spacing of restriction sites (eg. LpnPI).

There is a need for the development of improved methods to enable the identification of potential sites of differential methylation within a gene or genome that are amenable to subsequent methylation analysis, for example, for the purposes of disease diagnosis and/or prognosis.

SUMMARY OF THE INVENTION

Embodiments of the present invention provide a process for the efficient identification, on a genome-wide scale, of sites in the genome that are differentially methylated when comparing multiple samples.

One aspect of the present invention provides a method for identifying a site or region of a gene or genome for analysis, the method comprising:
 (a) obtaining one or more test samples of genomic DNA and one or more reference samples of genomic DNA;
 (b) digesting said test and reference samples with a methylation-dependent or methylation-sensitive restriction enzyme;
 (c) sequencing fragments obtained from step (b);
 (d) aligning sequences obtained from said test and reference samples with a reference genome;
 (e) comparing sequences obtained from said test and reference samples; and
 (f) identifying from the aligned sequences a methylated or unmethylated site or region of a gene or genome for analysis.

Another aspect of the invention provides a method for analysing methylation status of a site or region of a gene or genome, the method comprising:
 (a) obtaining one or more test samples of genomic DNA and one or more reference samples of genomic DNA;
 (b) digesting said test and reference samples with a methylation-dependent or methylation-sensitive restriction enzyme;
 (c) sequencing fragments obtained from step (b);

(d) aligning sequences obtained from said test and reference samples with a reference genome;
(e) comparing sequences obtained from said test and reference samples;
(f) identifying from the aligned sequences a methylated or unmethylated site or region of a gene or genome for analysis; and
(g) analysing the methylation status of said site or region in one or more additional samples.

BRIEF DESCRIPTION OF THE DRAWINGS

Embodiments of the invention are described herein, by way of non-limiting example only, with reference to the following figures.

DETAILED DESCRIPTION

The articles "a" and "an" are used herein to refer to one or to more than one (i.e., to at least one) of the grammatical object of the article. By way of example, "an element" means one element or more than one element.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

In the context of this specification, the term "about," is understood to refer to a range of numbers that a person of skill in the art would consider equivalent to the recited value in the context of achieving the same function or result.

The present inventors have recently developed two methods that allow selective amplification of target DNA sequences after restriction enzyme digestion. These methods, termed End-specific PCR, ESPCR (Rand and Molloy, 2010, and WO2007/109850; the disclosures of which are incorporated herein by reference) and Helper-Dependent Chain Reaction, HDCR (Rand et al., 2013, and WO2009/043112; the disclosures of which are incorporated herein by reference) both rely on an initial tagging step in which the free ends produced after enzyme digestion are extended on template oligonucleotides (Foligos or Helper oligonucleotides) to provide specific sequences at the ends of the molecules that can be used as priming sites for their amplification. HDCR incorporates additional features that provide for selectivity for target sequences in each cycle of amplification.

Recently a number of restriction enzymes have become available that cut DNA only when cytosines within their recognition sites are methylated (methylation-dependent enzymes). Thus, after enzyme digestion, free DNA ends are only produced when a particular site is methylated, providing the opportunity to positively select for amplification based on these cut ends. When combined with ESPCR or HDCR the use of methylation-dependent enzymes provide a means for selective amplification of methylated DNA without the requirement for bisulphite treatment and utilizing only nanogram amounts of DNA.

As described herein, the present inventors we have now developed methods that allow the efficient identification on a genome-wide scale of target restriction sites and fragments that provide targets for subsequent analysis, for example by sequence-selective amplification methods, such as via ESPCR and/or HDCR.

Figure 1:
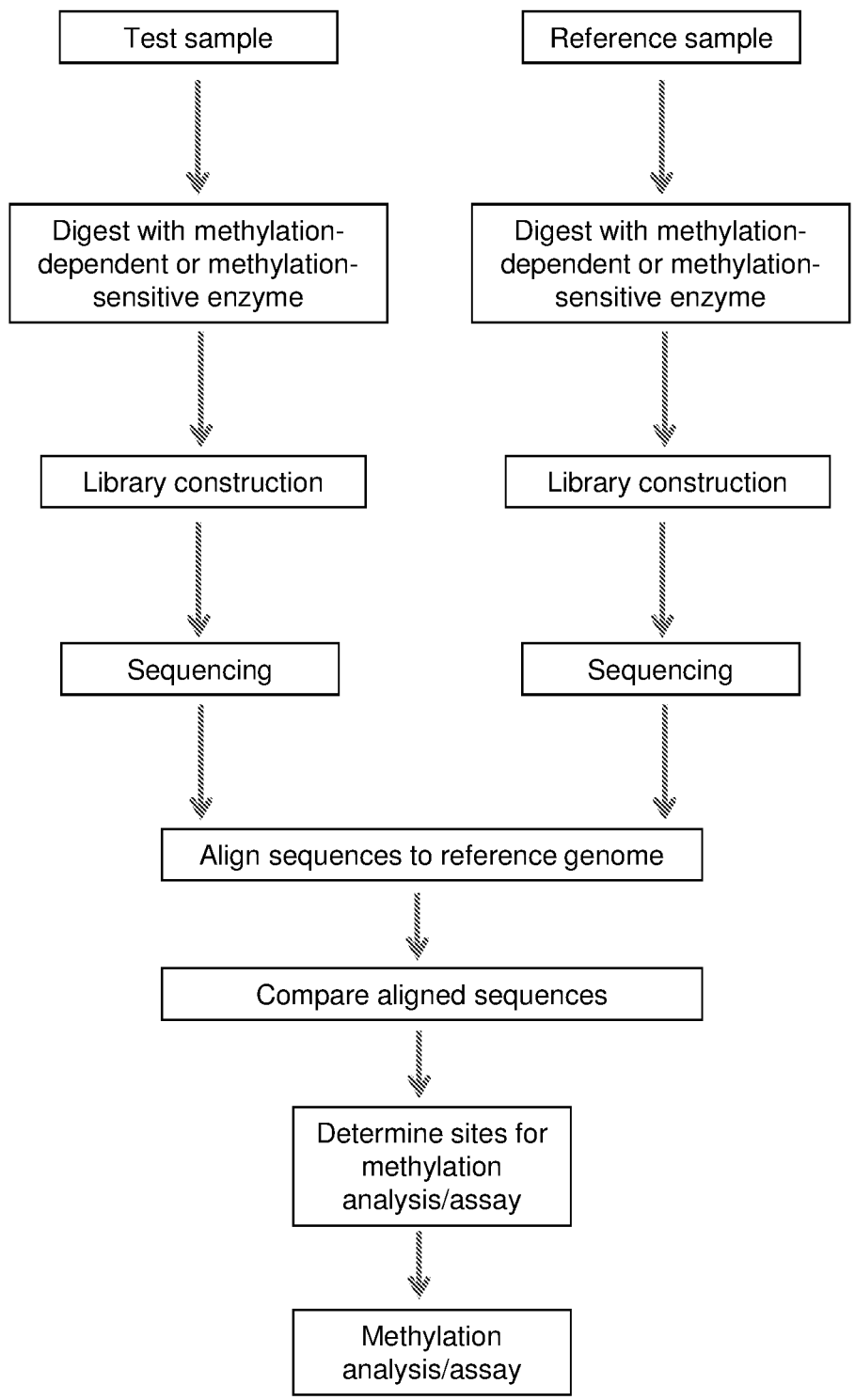
FIG. 1. Schematic flowchart of an exemplary method according to the present invention.

An exemplary method of the present invention is illustrated in FIG. 1. With reference to FIG. 1, the exemplary method comprises the following steps:

digesting DNA from one or more test samples and DNA from one or more reference samples with a methylation-sensitive or methylation-dependent restriction enzyme;

preparing libraries of restriction fragments generated and carrying out high throughput sequencing;

aligning and comparing sequences from the test sample and the reference sample, typically each being aligned separately to a reference genome prior to comparison; and identifying regions or sites of interest for subsequent assays or analysis.

Optionally, the method further comprises the development of an assay or method of analysis of identified regions or sites of interest. Such assays or methods of analysis may comprise amplification, for example typically sequence-selective amplification, of an identified region or site. Exemplary methods for sequence-selective amplification include HDCR and ESPCR as described hereinabove.

Optionally, after restriction enzyme digestion the method may comprise isolating a suitable size fraction of DNA fragments. For example, it may be desirable to size-select DNA fragments to facilitate subsequent analysis. In some embodiments the size-selected DNA fragments may be at least about 40 bp in length, up to about 500 bp in length. For optimal amplification efficiency, size-selected fragments may be between about 40 bp to about 150 bp, or between about 45 bp to about 120 bp. Size-selected fragments may be isolated, for example, by excision from a gel. Further, removal of repeat sequences from the library, for example by using biotinylated oligonucleotides for hybridisation-capture and removal may also be employed to allow excision to extend to smaller fragments suitable for amplification.

A reference genome is a database representing the complete genome for a species, typically assembled from DNA derived from multiple subjects. A number of suitable reference genomes are known to those skilled in the art. Exemplary human reference genomes include hg19, GRCh37 and GRCh38.

Identifying sequences that show substantially different numbers of reads between test sample and reference sample DNA, allows the data obtained from a method of the present invention to be used to select individual sites or fragments as targets for analysis, for example selective amplification by ESPCR or HDCR or other method of amplification. For example, as the target fragments sequenced and aligned to the genome are derived by cutting with the methylation-sensitive or methylation-dependent enzyme, regions identified by comparison of the aligned sequences from two or more libraries can be directly used for the development of ESPCR or HDCR assays.

Data generated using methods of the present invention can identify which sites are cut most efficiently and thus which sites would be preferred (amenable or most suitable) for analysis. By way of example, there is significant interest in the development of assays for detection of cancer-derived methylated DNA in plasma or serum, and a library prepared from white blood cell DNA (e.g. see Example 1) is particularly useful for identifying regions that show very low levels of methylation and therefore might be expected to provide low levels of background in blood-based assays.

Methods of the present invention find particular application in facilitating or enabling disease diagnosis or prognosis. For example, methods of the invention can be used to compare diseased and normal tissue to identify target regions for assay development, which regions may represent diagnostic or prognostic biomarkers of disease. Diseases may any disease associated with abnormal levels of methylation (undermethylation or overmethylation). Such diseases include, by way of example only, cancers such as colorectal cancer, conditions associated with aging such as Alzheimer's disease, metabolic diseases such as obesity, diabetes and metabolic syndrome, cardiovascular disease such as atherosclerosis and associated conditions, and arthritis.

For example, the MGMT gene is commonly methylated in a number of different cancers including colorectal cancer and gliomas, and MGMT methylation is used as a predicative biomarker for treatment with alkylating agents. As exemplified herein (see Example 2 and FIG. 2) profiles of MGMT methylation in colorectal cancer, and in in vitro fully methylated DNA compared to normal tissue and blood can be used to identify methylated regions of the gene suitable as targets for assay development.

In particular embodiments of the present methods the reference sample(s) may comprise DNA from one or more healthy subjects and the test sample(s) may comprise DNA from, for example one or more subjects suffering from a disease, predisposed to, or at risk of developing a disease, or suspected of having a disease; a disease. In other embodiments the reference and test samples may be derived from subjects representing different stages of the same disease. In other embodiments the reference and test samples may be derived from subjects that, in one group respond to a particular therapeutic agents or treatment and in the other group do not respond to the therapeutic agent or treatment.

The present invention provides a discovery pipeline, enabling the identification of multiple target sites and regions that display differential levels of methylation, simultaneously providing methylation-dependent (or sensitive) restriction enzyme cut sites and restriction fragments as targets for assay development.

A range of methylation-dependent and methylation-sensitive restriction enzymes with different recognition sites and cutting frequencies can be used to tailor the method for coverage of different methylation sites across a genome, providing flexibility to increase the number of samples analysed, without additional cost. The flexibility of enzyme choice also provides greater coverage of different genomic regions than is possible with other available reduced-representation methods, such as Illumina Human BeadChip450K (Sandoval et al., 2011) arrays and Reduced Representation Bisulphite Sequencing (RRBS; Meissner et al., 2008).

Identified restriction sites can be efficiently translated into diagnostic or prognostic assays using methylation-sensitive or methylation-dependent enzymes in combination with a range of available technologies, such as HDCR and ESPCR, or other technologies where the presence of specific sequences adjacent to the cut ends of a DNA fragment can be used to provide selectivity, such as NanoString (Geiss et al., 2008).

Such assays have the practical advantage of not requiring bisulphite-treatment of DNA. This can both reduce the time and cost of assays, material loss due to handling steps and ands can be readily applied to nanogram amounts of DNA such as might be obtained from clinical samples.

HDCR and ESPCR utilise both the presence of a cut end(s) and the sequence adjacent to the cut end(s) to allow addition of a tag sequence, and the amplification and detection of target fragments. However a number of alternate methods are available for adding tag sequences to cut ends. These include ligation of double-stranded linkers, ligation of single-stranded oligonucleotides to the denatured DNA fragments, either directly, or using a bridge oligonucleotide (as in NanoString, a modified application of which is exemplified herein) or using terminal transferase to add, for example, an oligo-dG sequence to the 3' end of a DNA strand. Any of these tagging methods, or variations or modifications thereto, can be used in combination with oligonucleotides within a target sequence region to provide specific amplification and/or detection of target sequences.

Incorporation of "universal" sequence tags or extensions to the target sequences by these methods enables subsequent capture, detection, amplification or analysis of the target, and provides the ability to use common outer primers for multiplexed amplification (e.g. ESPCR or HDCR) or capture of targets (e.g. NanoString). Sequence "tags" may comprise any suitable oligonucleotide sequence. As used herein the term "oligonucleotide" refers to a single-stranded sequence of ribonucleotide or deoxyribonucleotide bases, known analogues of natural nucleotides, or mixtures thereof.

An "oligonucleotide" comprises a nucleic-acid based molecule including DNA, RNA, PNA, LNA, UNA or any combination thereof. An oligonucleotide that predominantly comprises deoxyribonucleotide bases, natural or non-natural, may be referred to as a DNA oligonucleotide. Similarly, an oligonucleotide that predominantly comprises ribonucleotide bases, natural or non-natural, may be referred to as an RNA oligonucleotide. A DNA or RNA oligonucleotide need not include only standard DNA or RNA nucleobases, but may include one or more modified bases, such as for example inosine, methyl nucleotides, dideoxy nucleotides, 2'-O-flouro nucleotides, 2'-O-methoxyethyl nucleotides, universal nucleobases such as 5-nitro-indole, LNA, UNA, PNA and INA nucleobases, 2'-deoxy-2'-fluoro-arabinonucleic acid (FANA) and arabinonucleic acid (ANA). Oligonucleotides are typically short (for example less than 50, 60, 70 or 80 nucleotides in length) sequences that may be prepared by any suitable method, including, for example, direct chemical synthesis or cloning and restriction of appropriate sequences.

While methods of the present invention may be advantageously used in conjunction with ESPCR and HDCR or NanoString-based assays, those skilled in the art will recognise that the scope of the present invention not limited by reference to the downstream method or assay to be applied to the sites or regions identified by the present methods. By way of example only, the methods of the present invention may also be used to identify sites or regions for subsequent analysis by a range of other techniques such as methylation-specific PCR, HeavyMethyl PCR, Headloop PCR, MethylLight PCR, ConLight PCR, and COBRA (combined bisulphite restriction analysis). The skilled addressee will recognise other suitable means of analysis that may be employed as an alternative to, or in combination with, such amplification methods.

Where genomic regions of demethylation or undermethylation are desired to be identified, the restriction enzyme employed in the first step of a method of the present invention will typically be a methylation-sensitive enzyme. Suitable methylation-sensitive enzymes include, for example, HpaII and HhaI. However those skilled in the art will appreciate that the scope of the present invention is not so limited and other methylation-sensitive enzymes may be employed.

Where methylated genomic regions are desired to be identified, the restriction enzyme employed in the first step of the method will typically be a methylation-dependent enzyme. Suitable methylation-dependent enzymes include, for example, GlaI and LpnPI. However those skilled in the art will appreciate that the scope of the present invention is not so limited and other methylation-sensitive enzymes may be employed. By way of example only, suitable methylation-dependent enzymes include those listed in Table 1 Those skilled in the art will appreciate that this list is not necessarily comprehensive, and other methylation-dependent enzymes that may be, or become, known can also be employed.

(BWA) suite, or bowtie2, both of which construct output files in the common SAM (Sequence Alignment/Map) format, or in BAM, the binary compressed derivation of SAM. To sum across sequencing reads and determine the counts of reads at each genome coordinate it is simplest to use existing software which generates a table of metrics from sam or bam files; prominent examples being bedtools, or the R/Bioconductor libraries which use GenomicRanges. It is also common to process this table into a data format suitable for visualisation in a genome browser.

Ordering genome sites by the most differentially methylated regions requires, in a pairwise analysis, estimation of the magnitude of difference between sample sets A and B. In a biomarker discovery context, often the best sites for further inspection will have no methylation in one set (represented as zero read counts) and high methylation in the other set (represented as many read counts). A preferred comparison metric should be robust to zero containing count data. Ideally it should also limit the impact of technical artefacts which can result from incorrect alignment due to the incompleteness of the reference genome at telomeric or centromeric regions or misalignment of other repeat sequences.

Figure 2:
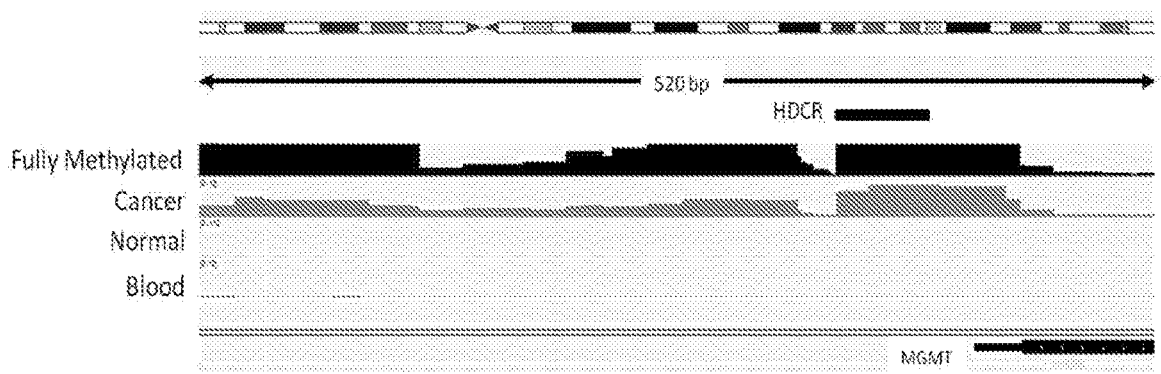
FIG. 2. Methylation profiles of MGMT (A) and RUNX3 (B) genes.
Figure 2:
Figure 3:
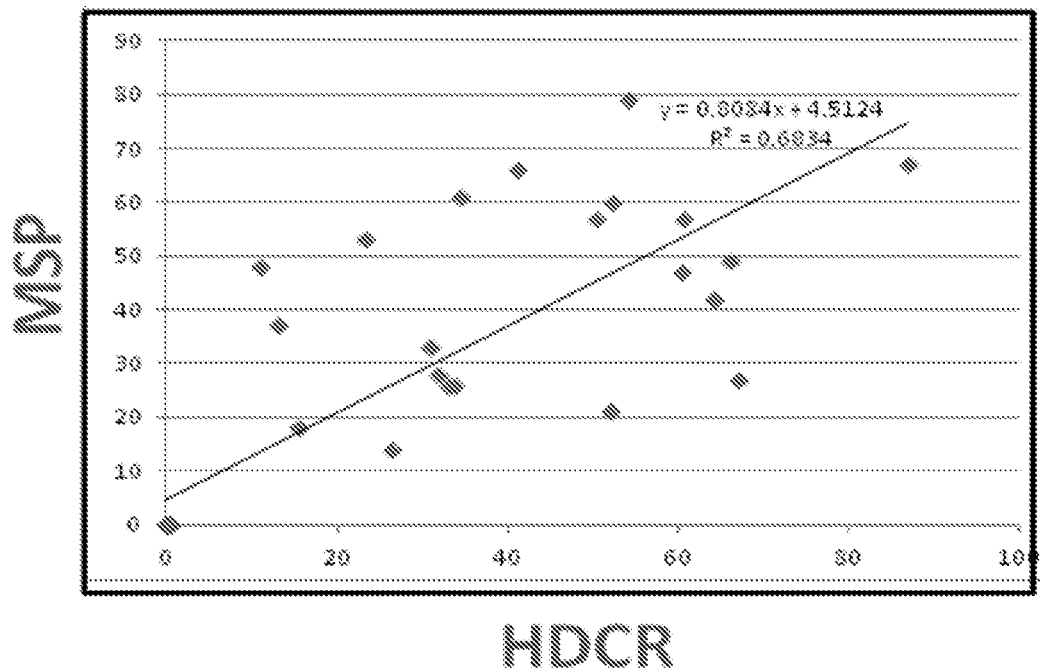
FIG. 3. Comparison of methylation status data from 40 colorectal cancer DNA samples obtained with a standard Methylation Specific PCR assay (MSP) versus data obtained with HDCR in accordance with an embodiment of the present invention.

Identification of regions most suitable or amenable for subsequent methylation analysis arising from the employment of methods of the invention may be based on visual inspection of histograms such as those shown in FIGS. 2 and 3. Alternatively, a computational/biostatistical approach may be adopted with the use of a specific algorithm(s). In the examples provide herein, in order to identify regions that showed differential DNA methylation between recurring and non-recurring cancers the following approach and algorithm was developed:

TABLE 1

Methylation-dependent restriction enzymes

| Enzyme | Supplier | Target Sites [#] | Mammalian (MG) Target Sites |
|---|---|---|---|
| GlaI | SibEnzyme | 5'-RMGY<br>3'-YGMR | 5'-GMGM(G)-3'<br>/3'-MGMG(C)-5' |
| PcsI | SibEnzyme | WMG(N)$_7$ MGW | WMG(N)$_7$ MGW |
| KroI | SibEnzyme | 5'-GCMGGC<br>3'-CGGMCG | 5'-GCMGGC<br>3'-CGGMCG |
| BlsI | SibEnzyme | 5'-RYNRY<br>3'-YRNYR | |
| LpnP1 | New England Biolabs (NEB) | 5'-CMDG-10/14 | 14/10-CMGG-10/14 |
| MspJI | NEB | 5'-MNNR-9/13 | MGNR-(9/13) forward<br>(13/9) YNMG reverse (MGNR on opposite strand) |
| FspE1 | NEB | CM-11/15 | CMG (11/15) Forward<br>(15/11) MGG Reverse (CMG on reverse strand) |
| McrBC | NEB | 5'-PuM(N$_{40-3000}$)PuM | |

[#] M = 5-methylcytosine

Where methylation-dependent enzymes are used in methods of the invention to identify regions of methylation, a methylation-sensitive enzyme may also be employed before, during or after digestion with the methylation-dependent enzyme to reduce or remove background.

The methods of the invention make use of known computational biology software and databases for the purposes of aligning, counting, comparison and analysis of sequence data. For example, suitable sequence alignment software includes an aligner from the Burrows-Wheeler Aligner 1. Calculate the log 2/base ratio between read coverage averages.
2. Zero read count regions produce inf/−inf values, which were replaced by the respective max/min values.
3. A weighted log-ratio was calculated as follows:

$$\log 2 \text{ coverage ratio} * (|covA-covB|/\sqrt{covA+covB})$$

4. The weighted log-ratio was normalised with the scale( ) function in R (http://www.R-project.org).

Those skilled in the art will recognise that alternative algorithms and computational/biostatistical approaches may also be developed for use in accordance with the present invention, depending upon the application to which the method is to be applied.

Embodiments of the invention described herein employ, unless otherwise indicated, conventional molecular biology known to, and within the ordinary skill of, those skilled the art.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present invention will now be described with reference to the following specific examples, which should not be construed as in any way limiting the scope of the invention.

Examples

Example 1—Exemplary Pipeline for Biomarker Assay Development

To provide a reference set of genome-wide data the inventors compared libraries of DNA fragments prepared following GlaI (Sibenzyme) digestion of human DNA that was methylated at all CpG sites (CpGenome, Millipore) or from pooled human white blood cell DNA (wbcDNA, Roche). GlaI was chosen because its recognition sites are reasonably frequent in the human genome, but also because its efficiency of cutting at potential target sites depends both on target site sequence composition as well as the number of cytosines that are methylated within the target site.

To prepare libraries, 1 µg of each DNA was digested at 30° C. with 4 units of GlaI for 2 hr in 50 µL. Following polyacrylamide gel electrophoresis, DNA in the size range of approximately 45 to 150 bp was isolated by gel excision and purified. This size range was chosen to encompass fragment sizes suitable for subsequent development of specific amplification reactions. The gel region excised extended from immediately above a prominent repeat sequence band arising from GlaI digestion of human DNA. The recovered, purified DNA was ligated with TruSeq linkers (Illumina) to generate sequencing libraries, following protocols provided by Illumina. Libraries were amplified for 10 cycles of PCR and 100 base single-end sequencing was performed on an Illumina HiSeq2500 sequencer.

Sequence read quality was assessed with FastQC (v 0.10.1) and all reads retained for subsequent analysis. Subsequently, the reads were aligned to a reference genome to determine the genome coordinates of the sequenced DNA.

Sequence reads were aligned to the human reference genome (hg19 build) with bowtie2 (v 2.1.0) using default parameters, except for '--very-sensitive-local' alignment using 15 threads. This strategy required no read trimming as the alignment algorithm performs soft-masking to align only relevant parts of the reads. The resultant bam files were sorted and indexed using samtools (v 0.1.19). Read counts were extracted using bedtools genomecov (v 2.19.1) and resultant bedgraph files converted to BigWig file format for display in the IGV browser using bedGraphToBigWig (v 4).

GlaI cut sites for display in the IGV browser were generated by in silico digest of the hg19 human reference genome sequence with the respective cut sites reported by SibEnzyme. (Note that one of the GlaI target sequences, GCAC, will not normally be methylated in the context of vertebrate CpG methylation.)

Plots of library reads across two genomic regions, comprising the MGMT and RUNX3 genes that are methylated in a fraction of colorectal cancers, are shown in FIG. 2. Histograms in the top and bottom tracks in each panel show the frequency of reads covering different genomic co-ordinates for both fully methylated DNA and wbcDNA respectively. Comparison of tracks shows that some regions are found to represented at similar levels in CpGenome and wbcDNA. In contrast, certain regions are present at high frequency in the CpGenome library, but are absent from the wbcDNA library, indicating low-level methylation in blood. Such regions are suitable for development of assays for detection of cancer-derived DNA in blood-based assays.

Example 2—MGMT and RU1VX3 Gene Analysis in Colorectal Cancer

Libraries were prepared from DNA from 20 colorectal cancer tissue samples and four samples of normal colorectal tissue. Libraries were prepared as in Example 1, except that a different barcode was used for each library to enable multiplexing. Sequences were aligned to the genome as in Example 1. The bedgraph format genome visualisation files of individual cancer samples were joined using bedtools unionbedg and coverage levels averaged.

Shown in the central tracks of the panels in FIG. 2 are the histograms of fragment reads across the MGMT and RUNX3 genes for the pooled cancer samples and pooled normal samples. It can be seen that as expected there is minimal methylation in normal colorectal tissue and extensive methylation in the cancer-derived DNA for both genes. The region of the MGMT gene indicated by the bar indicated above the 'fully methylated' histogram was used as a target for development of an efficient HDCR assay for detection of methylated MGMT sequences. The assay was designed with a HDCR Helper and Driver (Forward) oligonucleotides at one end of the GlaI fragment in combination with a standard reverse PCR primer. Oligonucleotide sequences are shown in Table 2.

TABLE 2

| | Sequence (5'-3')[1,2] | SEQ ID NO: |
|---|---|---|
| MGMT Fwd Helper | CICCITCCCTCTTTCTACAITGCG868TCTTGCTTTTC666T | 1 |
| Universal Fwd Driver | CCCGT5G55GT555T56665TA5AG | 2 |

TABLE 2-continued

| Sequence (5'-3')[1,2] | SEQ ID NO: |
|---|---|
| MGMT Reverse Primer   TGGGGCGGGGTCTAGAG | 3 |

[1]I = inosine; 5 = methylcytosine; 6 = O-methylthymine; 8 = O-methylcytosine
[2]The 3' four bases of the MGMT Helper (underlined) are mismatched with respect to the target and three (666) are O-methyl nucleotides to prevent extension Reaction components are set out in Table 3. HDCR was performed with the following cycling conditions: 15 cycles of 95°, 15 sec; 50°, 20 sec; 76°, 15 sec; 67°, 20 sec. This is followed by an amplification phase of 50 cycles of 95°, 5 sec; 60°, 20 sec; 76°, 15 sec; 67°, 20 sec.

TABLE 3

| Reagents | μL | Final concentration |
|---|---|---|
| GlaI digested DNA in SibEnzyme GlaI buffer | 4 | |
| 5 X Promega Go Taq Flexi Buffer | 3 | 1X |
| 50 mM MgCl$_2$ | 1.8 | 6 mM |
| 10 mM dNTPs | 0.3 | 200 nM |
| 5 μM Forward driver universal | 1.2 | 400 nM |
| 5 uM MGMT Forward Helper | 0.15 | 50 nM |
| 2 uM MGMT R1 primer | 0.1875 | 25 nM |
| 5 uM Probe MGMT | 0.15 | 50 nM |
| Platinum Taq 5 U/μL | 0.3 | 0.1 U/μL |
| Water (to make 15 μL final volume) | | |

The MGMT HDCR assay was applied to a set of 40 colorectal cancer DNA samples and data compared with that obtained using a standard Methylation Specific PCR assay (MSP) (Malley et al., 2011). Comparative data is plotted in FIG. 3. All 20 samples that tested positive by MSP also tested positive by HDCR, while 20 samples were negative in both assays.

Example 3—Differential Methylation in Recurring Cancers

Of the twenty subjects for whom GlaI libraries were prepared in Example 2, ten had cancers that recurred, while ten showed no recurrence. In order to identify regions of differential methylation that are associated with poorer outcome in subjects with Stage III colorectal cancer, the inventors compared library profiles in the two groups of subjects. Sequences were aligned to the genome as in Example 1. The bedgraph files of individuals in each group were joined using bedtools unionbedg and coverage levels averaged.

In order to identify regions that showed differential DNA methylation between cancers of recurring and non-recurring cancers the following approach was developed:
1. Calculate the log 2/base ratio between read coverage averages.
2. Zero read count regions produce inf/−inf values, which were replaced by the respective max/min values.
3. A weighted log-ratio was calculated as follows:

$$\text{log 2 coverage ratio} \cdot (|covA - covB|/\sqrt{covA + covB})$$

4. The weighted log-ratio was normalised with the scale( ) function in R (http://www.R-project.org).

Figure 4A:
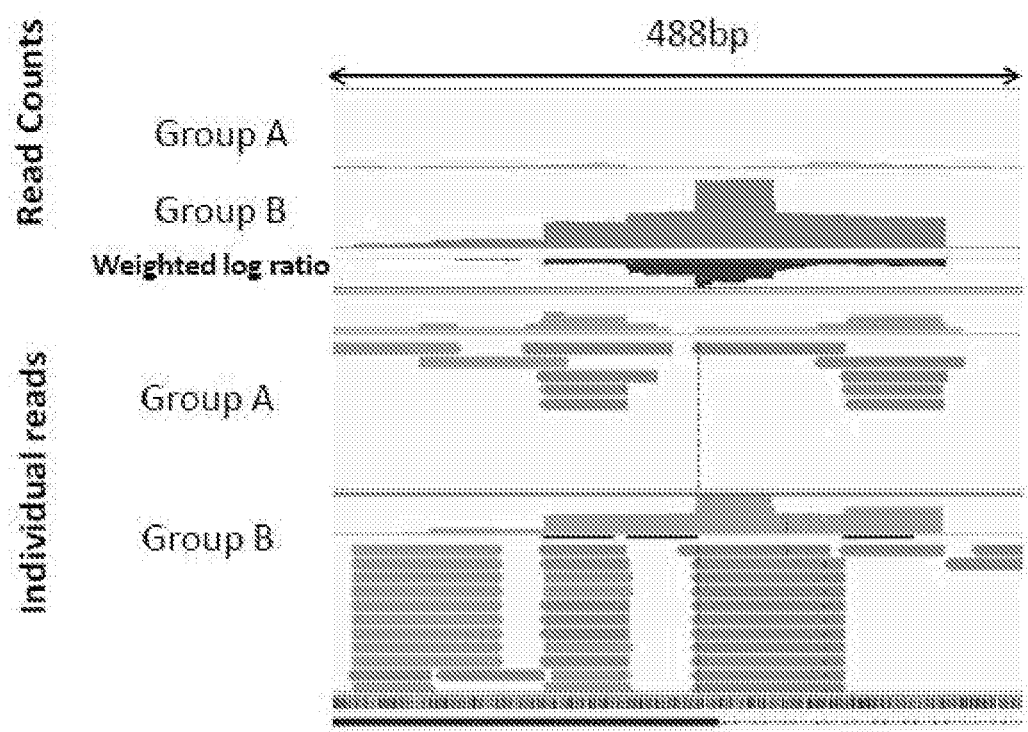
FIG. 4. Two genomic regions, one showing higher methylation (A) and one showing lower methylation (B) in recurring cancers. Sequence reads from individual clones are shown as left or right facing arrows depending on orientation. Histograms of read counts for recurring and non-recurring cancers and plots of the weighted log ratio of read counts are shown.
Figure 4B:
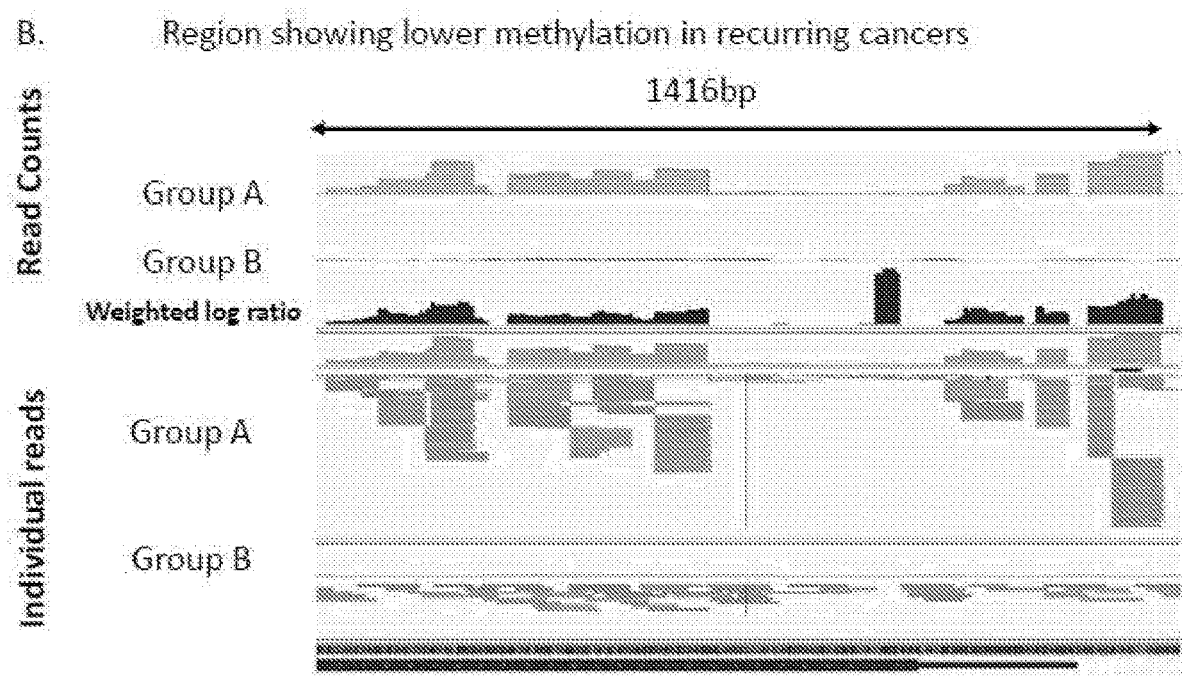

While a number of different approaches may be used to identify differentially methylated regions, we have chosen this approach as it enabled the identification of thousands of differentially methylated regions, which includes over 68,000 regions at a z-score>=5 cut-off. Of these, over 1,300 had relatively higher methylation in non-recurrent cancer samples, whereas more than 66,000 regions showed relatively higher methylation in progressing cancer subjects. Examples of two such regions are shown in FIG. 4.

Example 4—Modified NanoString Technology for Methylation Analysis

A modification of the NanoString technology offers one suitable assay method for methylation analysis in accordance with the present invention. In its normal use detection of individual nucleic acid molecules using NanoString technology (Geiss et al., 2008) is based on hybridisation of pairs oligonucleotides to target sequences, that provide bridges to a Universal Capture Tag and Reporter Tags that are specific to each target. One of the oligonucleotides contains an extended sequence that allows binding of a Universal Capture Tag containing a biotin moiety that allows the target molecule to be captured onto a streptavidin-containing surface. The other oligonucleotide anneals to a separate sequence in the target, containing a unique sequence-specific tag that allows binding of a Reporter Tag specific to the target sequence. After capture to the detection surface, the number of each captured target molecules is counted by reading the fluorescent barcodes on the Reporter Tags (http://www.nanostring.com/applications/technology).

Figure 5A:
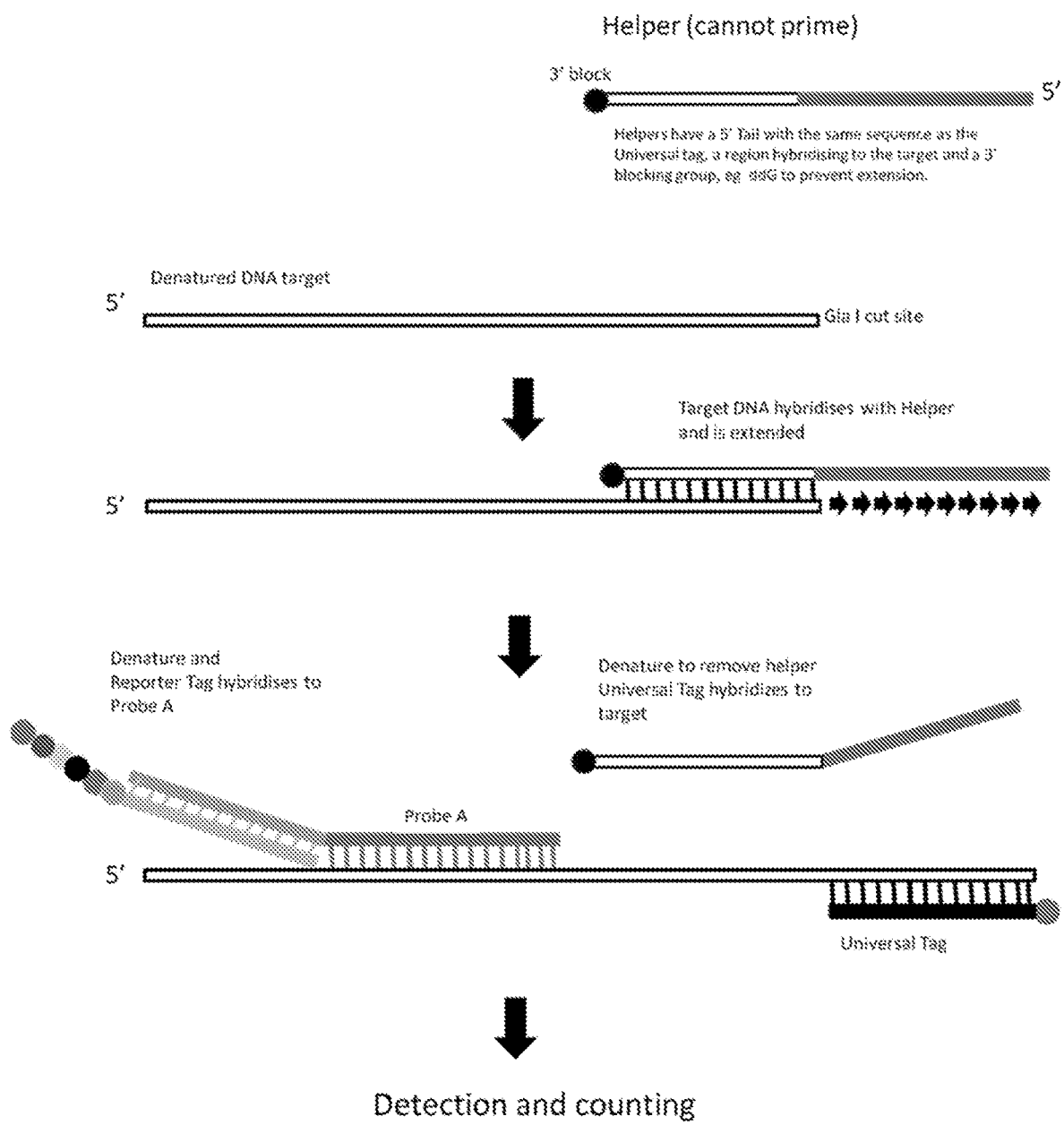
FIG. 5. Schematic diagram of an exemplary methylation detection technology based on NanoString, with single (A) and double (B) restriction enzyme cut sites. The Helper oligonucleotide has a 5' tail sequence (grey box) identical to the NanoString Universal Capture Tag, a region that hybridizes with the target DNA (open box) and a 3' blocking group (filled circle) to prevent extension.

This technology can be adapted for detection of methylated DNA sequences as described below and in FIG. 5. With reference to FIG. 5A, in order to detect methylation at a single restriction enzyme cut site, such as a GlaI site, the following steps may be used:
1. DNA is cut with GlaI and denatured, producing single-stranded target DNA.
2. A Helper oligonucleotide with sequence complementary to the 3' end of the GlaI restriction fragment is annealed to the single-stranded target DNA and the 3' end of the target primes extension of DNA synthesis using the Helper as template. The Helper oligonucleotide has a 5' tail sequence identical to the NanoString Universal Capture Tag, a region that hybridizes with the target DNA and a 3' blocking group, e.g. ddG to prevent extension.
3. This extended sequence is designed to allow hybridisation to the NanoString Universal Capture Tag.
4. A second oligonucleotide (Probe A) contains sequence complementary to the target DNA at its 5' end, with a 3' sequence extension that provides a unique tag sequence to allow hybridisation of a Reporter Tag.

Figure 5B:
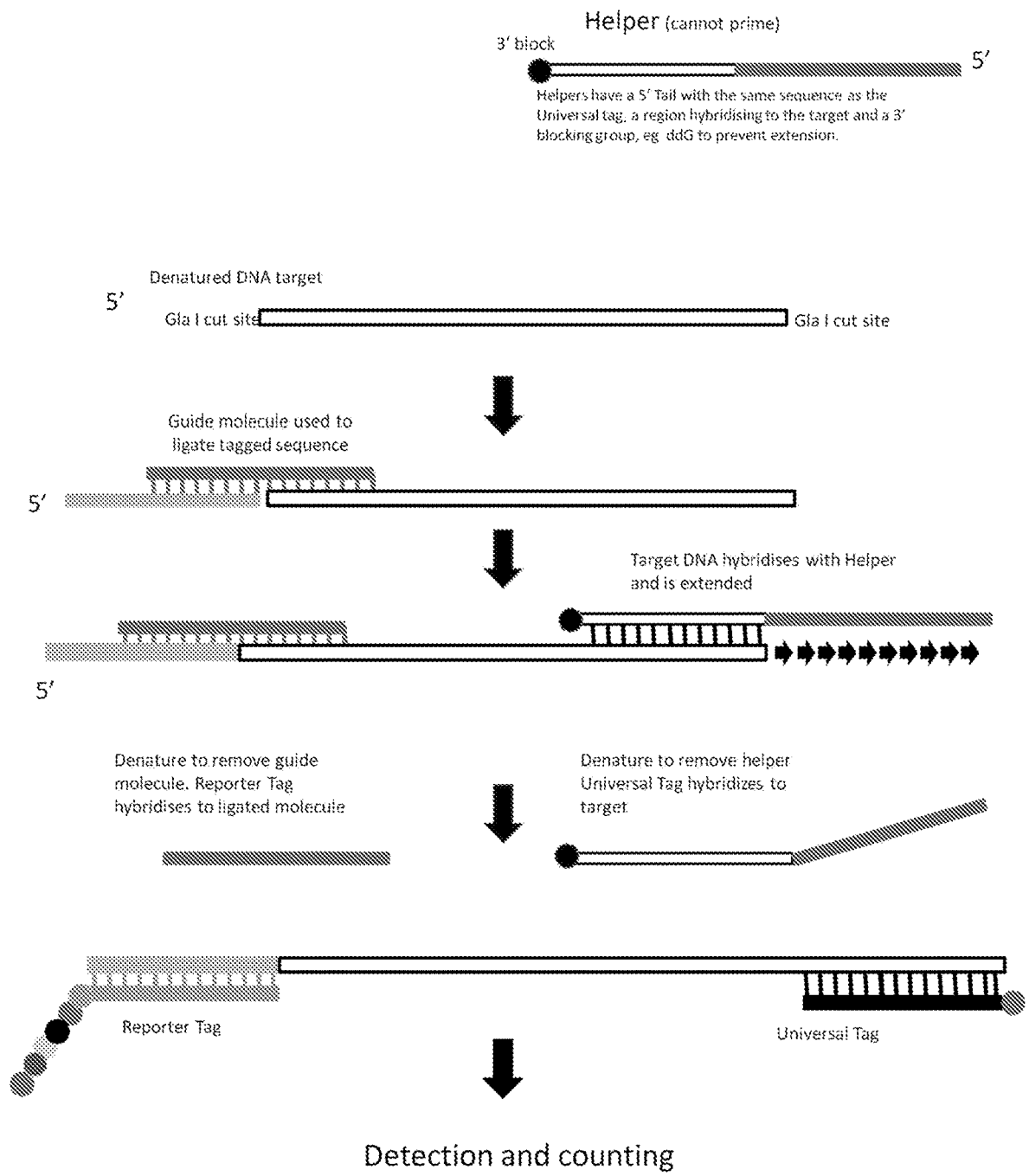

With reference to FIG. 5B, detection based on the two ends of a GlaI restriction fragment may employ the following steps:
1. DNA is cut with GlaI and denatured, producing single-stranded target DNA.

2. A Guide oligonucleotide is used to ligate a tag sequence to the 5' end of the target DNA.
3. A Helper oligonucleotide with sequence complementary to the 3' end of the target is annealed to the single-stranded target DNA and the 3' end of the target primes extension of DNA synthesis using the Helper as template. The Helper oligonucleotide has a 5' tail sequence identical to the NanoString Universal Capture Tag, a region that hybridizes with the target DNA and a 3' blocking group, e.g. ddG to prevent extension.
4. After melting off the Helper and Guide molecules, the NanoString Universal Capture Tag and Reporter Tags are annealed and used to detect target molecules.

REFERENCES

Clark S J, Statham A, Stirzaker C, Molloy P L & Frommer M. (2006) DNA methylation: Bisulphite modification and analysis. Nature Protocols 1:2353-2364.
Cottrell S E, Distler J, Goodman N S, Mooney S H, Kluth A, Olek A, Schwope I, Tetzner R, Ziebarth H, Berlin K. (2004) A real-time PCR assay for DNA-methylation using methylation-specific blockers. *Nucleic Acids Res.* 32, e10
Eads C A, Danenberg K D, Kawakami K, Saltz L B, Blake C, Shibata D, Danenberg P V, Laird P W. (2000) MethyLight: a high-throughput assay to measure DNA methylation. Nucleic Acids Res. 28, e32
Geiss G K, Bumgarner R E, Birditt B, Dahl T, Dowidar N, Dunaway D L, Fell H P, Ferree S, George R D, Grogan T, James J J, Maysuria M, Mitton J D, Oliveri P, Osborn J L, Peng T, Ratcliffe A L, Webster P J, Davidson E H, Hood L, Dimitrov K. (2008) Direct multiplexed measurement of gene expression with color-coded probe pairs. Nat Biotechnol.; 26:317-25.
Herman J G, Graff J R, Myöhänen S, Nelkin B D, Baylin S B. (1996) Methylation-specific PCR: a novel PCR assay for methylation status of CpG islands. *Proc Natl Acad Sci USA*. 93, 9821-9826.
Lofton-Day C, Model F, Devos T, Tetzner R, Distler J, Schuster M, Song X, Lesche R, Liebenberg V, Ebert M, Molnar B, Grützmann R, Pilarsky C, Sledziewski A. (2008) DNA methylation biomarkers for blood-based colorectal cancer screening. *Clin Chem.* 54,414-423.
Malley D S, Hamoudi R A, Kocialkowski S, Pearson D M, Collins V P, Ichimura K A (2011) distinct region of the MGMT CpG island critical for transcriptional regulation is preferentially methylated in glioblastoma cells and xenografts. Acta Neuropathol 121:651-61.
Meissner A, Mikkelsen T S, Gu H, Wernig M, Hanna J, Sivachenko A, Zhang X, Bernstein B E, Nusbaum C, Jaffe D B, et al. (2008) Genome-scale DNA methylation maps of pluripotent and differentiated cells. Nature, 454, 766-770.
Rand K, Qu W, Ho T, Clark S J & Molloy P L. (2002) Conversion-specific detection of DNA methylation using real-time polymerase chain reaction (ConLight-MSP) to avoid false positives. Methods 27:114-120.
Rand K N, Ho T, Qu W, Mitchell S M, White R, Clark S J, Molloy P L. (2005) Headloop suppression PCR and its application to selective amplification of methylated DNA sequences. *Nucleic Acids Res.* 33, e127.
Rand K N & Molloy P L. (2010) Sensitive measurement of unmethylated repeat DNA sequences by End-Specific PCR. Biotechniques 49(4):xiii-xvii.
Rand K N, Young G P, Ho T & Molloy P L. (2013) Sensitive and selective amplification of methylated DNA sequences using helper-dependent chain reaction in combination with a methylation-dependent restriction enzymes. *Nucleic Acids Res.* 41:e15.
Sandoval J, Heyn H A, Moran S, Serra-Musach J, Pujana M A, Bibikova M, Esteller M. Validation of a DNA methylation microarray for 450,000 cpg sites in the human genome. (2011) *Epigenetics-Us* 6, 692-702.
Weisenberger D J, Siegmund K D, Campan M, Young J, Long T I, Faasse M A, Kang G H, Widschwendter M, Weener D, Buchanan D, Koh H, Simms L, Barker M, Leggett B, Levine J, Kim M, French A J, Thibodeau S N, Jass J, Haile R, Laird P W. (2006) CpG island methylator phenotype underlies sporadic microsatellite instability and is tightly associated with BRAF mutation in colorectal cancer. *Nat Genet.* 38, 787-793.

The invention claimed is:

1. A method for identifying a site or region of a gene or genome for differential methylation analysis, the method comprising:
   (a) obtaining one or more test samples of genomic DNA and one or more reference samples of genomic DNA;
   (b) digesting said samples of genomic DNA obtained in (a) with a methylation-dependent restriction enzyme selected from GlaI, PcsI, KroI and combinations thereof;
   (c) selecting restriction fragments generated in (b) of between about 40 bp and 500 bp;
   (d) constructing libraries of said selected restriction fragments;
   (e) sequencing said libraries;
   (f) aligning said sequences obtained in (e) and derived from said samples of genomic DNA with a reference genome;
   (g) comparing sequences consisting of said sequences aligned in (f); and (h) identifying a methylated or unmethylated site or region of a gene or genome within the test sample of genomic DNA from said comparing of sequences.

2. A method according to claim 1, wherein the digestion of step (b) generates one or more fragments with a single end cut by the restriction enzyme.

3. A method according to claim 1, wherein the digestion of step (b) generates one or more fragments with both ends cut by the restriction enzyme.

4. A method according to claim 1, wherein said one or more test samples comprise genomic DNA from one or more disease cells or tissues.

5. A method according to claim 4, wherein the disease is selected from cancer, a metabolic disease, a cardiovascular disease, a disease associated with aging, and arthritis.

6. A method according to claim 1, wherein said one or more test samples comprise genomic DNA from one or more individuals suspected of suffering from a disease or at risk of developing a disease.

7. A method according to claim 1, wherein said analysis comprises selective detection and/or amplification of a target sequence(s).

8. A method according to claim 7, wherein said selective detection comprises a step of adding a sequence tag at one or both cut end(s) of the digested fragments to facilitate subsequent analysis.

9. A method according to claim 1, wherein said analysis comprises a diagnostic or prognostic assay for a disease.

10. A method for analysing methylation status of a site or region of a gene or genome, the method comprising:
    (a) obtaining one or more test samples of genomic DNA and one or more reference samples of genomic DNA;
    (b) digesting said samples of genomic DNA obtained in (a) with a methylation-dependent restriction enzyme selected from GlaI, PcsI, KroI and combinations thereof;
    (c) selecting restriction fragments generated in (b) of between about 40 bp and 500 bp;
    (d) constructing libraries of said selected restriction fragments;
    (e) sequencing said libraries;
    (f) aligning said sequences obtained in (e) and derived from said samples of genomic DNA with a reference genome;
    (g) comparing sequences consisting of said sequences aligned in (f);
    (h) identifying a methylated or unmethylated site or region of a gene or genome within the test sample of genomic DNA from said comparing of sequences; and
    (i) analysing the methylation status of said site or region in one or more additional samples.

11. A method according to claim 10, wherein the digestion of step (b) generates one or more fragments with a single end cut by the restriction enzyme.

12. A method according to claim 10, wherein the digestion of step (b) generates one or more fragments with both ends cut by the restriction enzyme.

13. A method according to claim 10, wherein said one or additional samples are derived from subjects of interest.

14. A method according to claim 10, wherein said analysis comprises a diagnostic or prognostic assay for a disease.

15. A method according to claim 10, wherein said analysis comprises selective detection and/or amplification of said site or region.

16. A method according to claim 15, wherein said selective detection comprises a step of adding a sequence tag at the one or both cut end(s) of the digested fragments to facilitate subsequent analysis.

* * * * *

SEQUENCE LISTING

```
<160> NUMBER OF SEQ ID NOS: 3

<210> SEQ ID NO 1
<211> LENGTH: 42
<212> TYPE: DNA
<213> ORGANISM: Artificial Sequence
<220> FEATURE:
<223> OTHER INFORMATION: Synthetic sequence
<220> FEATURE:
<221> NAME/KEY: modified_base
<222> LOCATION: (2)..(2)
<223> OTHER INFORMATION: I
<220> FEATURE:
<221> NAME/KEY: modified_base
<222> LOCATION: (5)..(5)
<223> OTHER INFORMATION: I
<220> FEATURE:
<221> NAME/KEY: modified_base
<222> LOCATION: (20)..(20)
<223> OTHER INFORMATION: I
<220> FEATURE:
<221> NAME/KEY: modified_base
<222> LOCATION: (25)..(25)
<223> OTHER INFORMATION: O-methylcytosine
<220> FEATURE:
<221> NAME/KEY: modified_base
```

```
<222> LOCATION: (26)..(26)
<223> OTHER INFORMATION: O-methylthymine
<220> FEATURE:
<221> NAME/KEY: modified_base
<222> LOCATION: (27)..(27)
<223> OTHER INFORMATION: O-methylcytosine
<220> FEATURE:
<221> NAME/KEY: modified_base
<222> LOCATION: (39)..(41)
<223> OTHER INFORMATION: O-methylthymine

<400> SEQUENCE: 1
caccatccct ctttctacaa tgcgctctct tgcttttctt tt                             42

<210> SEQ ID NO 2
<211> LENGTH: 25
<212> TYPE: DNA
<213> ORGANISM: Artificial Sequence
<220> FEATURE:
<223> OTHER INFORMATION: Synthetic sequence
<220> FEATURE:
<221> NAME/KEY: modified_base
<222> LOCATION: (6)..(6)
<223> OTHER INFORMATION: methylcytosine
<220> FEATURE:
<221> NAME/KEY: modified_base
<222> LOCATION: (8)..(9)
<223> OTHER INFORMATION: methylcytosine
<220> FEATURE:
<221> NAME/KEY: modified_base
<222> LOCATION: (12)..(14)
<223> OTHER INFORMATION: methylcytosine
<220> FEATURE:
<221> NAME/KEY: modified_base
<222> LOCATION: (16)..(16)
<223> OTHER INFORMATION: methylcytosine
<220> FEATURE:
<221> NAME/KEY: modified_base
<222> LOCATION: (17)..(19)
<223> OTHER INFORMATION: O-methylthymine
<220> FEATURE:
<221> NAME/KEY: modified_base
<222> LOCATION: (20)..(20)
<223> OTHER INFORMATION: methylcytosine
<220> FEATURE:
<221> NAME/KEY: modified_base
<222> LOCATION: (23)..(23)
<223> OTHER INFORMATION: methylcytosine

<400> SEQUENCE: 2
cccgtcgccg tccctctttc tacag                                               25

<210> SEQ ID NO 3
<211> LENGTH: 17
<212> TYPE: DNA
<213> ORGANISM: Artificial Sequence
<220> FEATURE:
<223> OTHER INFORMATION: Synthetic sequence

<400> SEQUENCE: 3
tggggcgggg tctagag                                                        17
```